(12) United States Patent
Eliott et al.

(10) Patent No.: US 10,828,306 B2
(45) Date of Patent: Nov. 10, 2020

(54) METHOTREXATE FOR PROLIFERATIVE VITREORETINOPATHY

(71) Applicant: Massachusetts Eye and Ear Infirmary, Boston, MA (US)

(72) Inventors: Dean Eliott, Carlsbad, CA (US); Tomasz P. Stryjewski, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 16/397,562

(22) Filed: Apr. 29, 2019

(65) Prior Publication Data

US 2020/0085827 A1    Mar. 19, 2020

Related U.S. Application Data

(63) Continuation of application No. 15/699,559, filed on Sep. 8, 2017, now Pat. No. 10,272,089, which is a continuation of application No. 15/500,351, filed as application No. PCT/US2015/042951 on Jul. 30, 2015, now Pat. No. 10,098,884.

(60) Provisional application No. 62/030,778, filed on Jul. 30, 2014.

(51) Int. Cl.
  *A61K 9/00*    (2006.01)
  *A61K 31/519*  (2006.01)
  *A61K 9/50*    (2006.01)

(52) U.S. Cl.
  CPC ............ *A61K 31/519* (2013.01); *A61K 9/00* (2013.01); *A61K 9/0019* (2013.01); *A61K 9/0048* (2013.01); *A61K 9/0051* (2013.01); *A61K 9/5026* (2013.01); *A61K 9/5047* (2013.01)

(58) Field of Classification Search
  CPC .................................................... A61K 9/5026
  See application file for complete search history.

(56) References Cited

U.S. PATENT DOCUMENTS

| 2004/0253243 A1 | 12/2004 | Epstein |
| 2005/0255144 A1 | 11/2005 | Schultz |
| 2006/0002963 A1 | 1/2006 | Rabinovich-Guilatt et al. |
| 2006/0073182 A1 | 4/2006 | Wong et al. |
| 2008/0038316 A1 | 2/2008 | Wong et al. |
| 2008/0241221 A1 | 10/2008 | Whitcup et al. |
| 2009/0081277 A1 | 3/2009 | Robinson |
| 2009/0093414 A1 | 4/2009 | Ikeya |

(Continued)

FOREIGN PATENT DOCUMENTS

| JP | 2003-518987 | 6/2003 |
| WO | WO 0149226 | 7/2001 |

(Continued)

OTHER PUBLICATIONS

Banerjee et al, Trials vol. 14, Article No. 42 (2013). (Year: 2013).*

(Continued)

*Primary Examiner* — Benjamin J Packard
(74) *Attorney, Agent, or Firm* — Fish & Richardson P.C.

(57) ABSTRACT

The use of methotrexate, e.g., repeated dosing or sustained-release formulations of methotrexate, for treating or reducing risk of proliferative vitreoretinopathy (PVR) or epiretinal membranes (ERM), e.g., after surgical vitrectomy to treat retinal detachment.

22 Claims, 4 Drawing Sheets

(56) References Cited

U.S. PATENT DOCUMENTS

| | | |
|---|---|---|
| 2011/0200662 A1 | 8/2011 | Glazier |
| 2012/0263779 A1 | 10/2012 | Lyons et al. |
| 2014/0105956 A1 | 4/2014 | Banerjee et al. |

FOREIGN PATENT DOCUMENTS

| | | |
|---|---|---|
| WO | WO 2011/1143484 | 11/2011 |
| WO | WO 2014/074823 | 5/2014 |

OTHER PUBLICATIONS

Hardwig et al, American Journal of Ophthalmology, vol. 142, Issue 5, 883-885, 2006. (Year: 2006).*

Ahmadieh et al. "Triamcinolone Acetonide in Silicone-Filled Eyes as Adjunctive Treatment for Proliferative Vitreoretinopathy," Ophthalmology 2008, 115:1938-1943.

Asaria et al., "Adjuvant 5-fluorouracil and heparin prevents proliferative vitreoretinopathy : Results from a randomized, double-blind, controlled clinical trial," Ophthalmology, Jul. 2001, 108(7):1179-83.

Bae et al., "Effect of Intravitreal Methotrexate and Aqueous Humor Cytokine Levels in Refractory Retinal Vasculitis in Behcet Disease," Retina, Jul. 2012, 32: 1395-1402.

Barron et al., "Intravitreal methotrexate as an adjunctive treatment of intraocular lymphoma," Archives of Opthalmology, Sep. 1997, 115: 1152-1156.

Blumenkranz and Hartzer, "Chapter 132—Section 3: Special Adjuncts to Treatment—The Mechanism of Action of Drugs for the Treatment of Vitreoretinal Scarring," Retina, 2006, 2242-2253.

Blumenkranz et al., "Selection of therapeutic agents for intraocular proliferative disease," Arch Opthalmol, 102: 598-604, 1984.

Bonetti et al., "An extended-release formulation of methotrexate for subcutaneous administration,"Cancer Chemother Pharmacol, 1994, 33:303-306.

Bong et al., "Attitudes of patients and relatives/carers towards genetic testing for inherited retinal disease," Eye, 2010, 24: 1622-1625.

Bordaberry and Marcela, "Vogt-Koyanagi-Harada disease: diagnosis and treatments update," Curr Opin Ophthalmol, Nov. 2010, 21: 430-435.

Cardillo, "An intravitreal biodegradable sustained release naproxen and 5-fluorouracil system for the treatment of experimental post-traumatic proliferative vitreoretinopathy," British Journal of Ophthalmology, 2004, 88:1201-1205.

Cavalcante et al., "Intravitreal injection analysis at the Bascom Palmer Eye Institute: evaluation of clinical indications for the treatment and incidence rates of endophthalmitis," Clin Ophthalmol, May 2010,4:519-24.

Chandler et al., "The effect of triamcinolone acetonide on a refined experimental model of proliferative vitreoretinopathy," American Journal of Ophthalmology, 1985, 99(6): 686-690.

Chatelut et al., "Sustained-release methotrexate for intracavitary chemotherapy," J Pharm Sci, Mar. 1994, 83(3):429-32.

Cheema et al., "Triamcinolone acetonide as an adjuvant in the surgical treatment of retinal detachment with proliferative vitreoretinopathy," Ophthalmic Surg Lasers Imaging, 2007, 38(5): 365-370.

Chen et al., "Midterm results of low-dose intravitreal triamcinolone as adjunctive treatment for proliferative vitreoretinopathy," Retina, 2011, 31: 1137-1142.

Chen et al., "The effect of combined daunorubicin and triamcinolone acetonide treatment on a refined experimental model of proliferative vitreoretinopathy," Investigative Ophthalmology & Visual Science, 1992, 33(7): 2160-2164.

Cheng et al., "Intravitreal sustained-release dexamethasone device in the treatment of experimental uveitis," Invest. Opthalmol. Vis. Sci, 1995, 36:442-53.

Constable and Nagpal, "Chapter 107—Section 3: Complicated forms of retinal detachment—Proliferative Vitreoretinopathy," 2013, 1806-1825.

Creten et al., "Systemic resorption of 5-fluorouracil used in infusion fluid during vitrectomy," Bull Soc Belge Ophthalmol, 2007, 303: 35-39.

De Smet et al., "Intravitreal chemotherapy for the treatment of recurrent intraocular lymphoma," Br F Ophthalmol, 1999, 83: 448-451.

Eliott, "Chapter 10: Transvitreal chorioretinal Biopsy," In Elliott and Rao, Eds. Surgical Management of Intraocular Inflammation and Infection, 2013, 11 pages.

Eliott, "Methotrexate in the management of retinal detachment: a pilot study," Informed Consent, Massachusetts Eye and Ear Infirmary, Mar. 2012-Mar. 2013, 8 pages.

Extended European Search Report in Application No. 15827946.3, dated Mar. 5, 2018, 9 pages.

Fishburne et al., "Intravitreal methotrexate as an adjunctive treatment of intraocular lymphoma," Arch Ophthalmol, 1997, 115:1152-1156.

Frenkel et al., "Intravitreal methotrexate for treating vitreoretinal lymphoma: 10 years of experience," Br J Ophthalmol , 2008, 92: 383-388.

Genestier et al. "Immunosuppressive properties of methotrexate: apoptosis and clonal deletion of activated peripheral T cells," J Clin Invest, 1998, 102:322-328.

Gerards et al., "Inhibition of cytokine production by methotrexate: Studies in healthy volunteers and patients with rheumatoid arthritis," Rheumatology, 2003, 42:1189-1196.

Haghjou et al., "Sustained release intraocular drug delivery devices for treatment of uveitis," J Ophthalmic Vis Res, 2011, 6(4):317-329.

Hardwig et al., "Intraocular methotrexate in ocular diseases other than primary central nervous system lymphoma," American Journal of Ophthalmology, 2006, 142: 883-885.

Hardwig et al., "The safety of intraocular methotrexate in silicone-filled eyes," Retina, 2008, 8:1082-1086.

Hong et al., "Ocular involvement in patients with primary CNS lymphoma," J Neurooncol, 2011, 102: 139-145.

International Search Report and Written Opinion in International Application No. PCT/US15/42951, dated Nov. 2, 2015.

Johnston et al., "The anti-inflammatory action of methotrexate is not mediated by lymphocyte apoptosis, but by the suppression of activation and adhesion molecules," Clin Immunol, 2005, 114:154-163.

Jonas et al., "Intravitreal injection of crystalline cortisone as adjunctive treatment of proliferative vitreoretinopathy," British Journal of Ophthalmology, 2000, 84(9): 1064-1067.

Kim et al., "Controlled drug release from an ocular implant: an evaluation using dynamic three-dimensional magnetic resonance imaging," Invest. Ophthalmol. Vis. Sci, 2004, 45(8):2722-2731.

Kivela et al., "Intravitreal methotrexate for retinoblastoma," Ophthalmology, 118: 8, 2011.

Kolomeyer et al., "The Use of Intravitreal Ranibizumab for Choroidal Neovascularization Associated with Vogt-Koyanagi-Harada Syndrome," Case Reports in Medicine, Aug. 2011, 2011: 747648.

Kurup et al., "Intravitreal methotrexate in therapeutically resistant exudative age-related macular degeneration," Acta Opthalmologica, e145-e146, 2010.

Lean et al., "Classification of proliferative vitreoretinopathy used in the silicone study," The Silicone study group, Ophthalmology, 1989, 96:765-771.

Lee et al., "Biodegradable implants for sustained drug release in the eye," Pharm Res. 27(10):2043-53, 2010.

Machemer et al., "An updated classification of retinal detachment with proliferative vitreoretinopathy," Am J Ophthalmol, Aug. 1991, 112:159-65.

Meyer et al., "Incidence of rhegmatogenous retinal detachments after intravitreal antivascular endothelial factor injections," Acta Ophthalmol, Feb. 2011, 89(1):70-5.

Mietz et al., "Onset and recurrence of proliferative vitreoretinopathy in various vitreoretinal disease," British Journal of Ophthalmology, 1995, 79:874-877.

(56) References Cited

OTHER PUBLICATIONS

Montesinos et al., "Reversal of the antiinflammatory effects of methotrexate by the nonselective adenosine receptor antagonists theophylline and caffeine: Evidence that the antiinflammatory effects of methotrexate are mediated via multiple adenosine receptors in rat adjuvant arthritis," Arthritis Rheum, 2000, 43:656-663.
Munir al., "Intravitreal triamcinolone for treatment of complicated proliferative diabetic retinopathy and proliferative vitreoretinopathy," Can J Ophthalmol, 2005, 40:598-604.
Office Action in Japanese Application No. 2017-505180, dated Apr. 9, 2019, 7 pages (with English translation).
Owen et al. "Abstract # 1179/D826: Preliminary Results of Treatment With Intravitreal Methotrexate in Patients With Macula Oedema Secondary to Uveitis," Presented at the Association for Research in Vision and Ophthalmology Annual Meeting, United Kingdom, May 2012, 2 pages.
Palakurthi et al., "Investigation of kinetics of methotrexate for therapeutic treatment of intraocular lymphoma," Current Eye Research, 2010, 35(12):1105-1115.
Palakurthi et al., "Toxicity of a biodegradable microneedle implant loaded with methotrexate as a sustained release device in normal rabbit eye: a pilot study," J Ocul Pharmacol Ther, 2011, 27:151-156.
Partial European Supplementary Search Report in Application No. 15827946.3, dated Dec. 1, 2017, 11 pages.
Pastor et al., "Proliferative vitreoretinopathy: risk factors and pathobiology," Progress in Retinal and Eye Research, 2002, 21:127-144.
Pastor, "Proliferative Vitreoretinopathy: An Overview," Survey of Ophthalmology, Jul.-Aug. 1998, 43:3-18.
Pennock et al., "A novel strategy to develop therapeutic approaches to prevent proliferative vitreoretinopathy," Am J Pathol, Dec. 2011, 179(6):2931-40.
Retina Society Terminology Committee, "The classification of retinal detachment with proliferative vitreoretinopathy," Ophthalmology, Feb. 1983, 90:121-5.
Samson et al., "Methotrexate therapy for chronic noninfectious uveitis: analysis of a case series of 160 patients," Ophthalmology, Jun. 2001, 108(6):1134-9.
Schiff et al., "Safety and efficacy assessment of chimeric ribozyme to proliferating cell nuclear antigen to prevent recurrence of proliferative vitreoretinopathy," Arch Ophthalmol, Sep. 2007, 12:1161-7.
Seitz et al., "Enhanced in vitro induced production of interleukin 10 by peripheral blood mononuclear cells in rheumatoid arthritis is associated with clinical response to methotrexate treatment," J Rheumatol, 2001, 28:496-501.
Sijssens et al., "Long-term ocular complications in aphakic versus pseudophakic eyes of children with juvenile idiopathic arthritis-associated uveitis," Br J Ophthalmol, Sep. 2010, 94:1145-9.
Smith et al., "Role of intravitreal methotrexate in the management of primary central nervous system lymphoma with ocular involvement," Ophthalmology, 109: 9, 1709-1716, 2002.
Soheilian et al., "Pilot study of safety and effect of combined intravitreal bevacizumab and methotrexate for neovascular age-related macular degeneration," Eur J Ophthalmol, 2011, 21: 77-82.
Sou et al., "Treatment of primary intraocular lymphoma with intravitreal methotrexate," Jpn J Ophthalmol, 2008, 52:167-174.
Stryjewski, "Proliferative Vitreoretinopathy After Retinal Detachment: New Understandings of Risk, New Opportunities for Prevention," Thesis for the degree of M.D., Harvard Medical School, Jan. 2013, 100 pages.
Sunalp et al., "Effects of cytotoxic drugs on proliferative vitreoretinopathy in the rabbit cell injection model," Current Eye Research, 2009, 3: 619-623.
Sundaram et al., "Intravitreal low molecular weight heparin and 5-Fluorouracil for the prevention of proliferative vitreoretinopathy following retinal reattachment surgery," Cochrane Database of Systematic Reviews, 2010, (7): CD006421.
Taheri et al., "Nanoparticles of Conjugated Methotrexate-Human Serum Albumin. Preparation and Cytotoxicity Evaluations," J Nanomaterials, 2011, 2011: Article ID 768201, 7 pages.
Taylor et al., "Intraocular Methotrexate in the Treatment of Uveitis and Uveitic Cystoid Macular Edema," Ophthalmology, 2009, 116:797-801.
Velez and Whitcup, "New developments in sustained release drug delivery for the treatment of intraocular disease," Br J Ophthalmol, 1999, 83:1225-1229.
Velez et al., "Pharmacokinetics and toxicity of intravitreal chemotherapy for primary intraocular lymphoma," Arch Ophthalmol, 2001, 119: 1518-1524, 2001.
Vijayaragavan et al., "Controlled Release of Methotrexate Using Alpha-Lactalbumin Microparticles," Int J Pharm Res, 2011, 3(1):39-44.
Wickham et al., "Surgical failure following primary retinal detachment surgery by vitrectomy: risk factors and functional outcomes," Br J Ophthalmol, Sep. 2011, 95(9):1234-8.
Wiedemann et al., "Adjunctive daunorubicin in the treatment of proliferative vitreoretinopathy: results of a multicenter clinical trial," Daunomycin Study Group, Am J Ophthalmol, 1998, 126(4):550-9.
Wiedemann et al., Chapter 97—Section 1: The Pathophysiology of Retinal Detachment and Associated Problems—Pathogenesis of Proliferative Vitreoretinopathy, 2013, 1641-1646.
Yang et al., "An intravitreal sustained-release triamcinolone and 5-fluorouracil codrug in the treatment of experimental proliferative vitreoretinopathy," Arch Ophthalmol 1998;116:69-77.
Yeh et al. "Combination intravitreal rituximab and methotrexate for massive subretinal Lymphoma," Eye, 2010, 24: 1625-1627.
JP Office Action in Japanese Application No. 2017-505180, dated Nov. 11, 2019, 7 pages (with English translation).
JP Office Action in Japanese Application No. 2017-505180, dated Aug. 11, 2020, 7 pages (with English translation).

\* cited by examiner

METHOTREXATE FOR PROLIFERATIVE VITREORETINOPATHY

CLAIM OF PRIORITY

This application is a continuation of U.S. patent application Ser. No. 15/699,559, filed Sep. 8, 2017, now U.S. patent Ser. No. 10/272,089, which is a continuation of U.S. patent application Ser. No. 15/500,351, filed on Jan. 30, 2017, now U.S. Pat. No. 10,098,884, which is the US National Stage under § 371 of International Application No. PCT/US2015/042951, filed Jul. 30, 2015, which claims the benefit of U.S. Patent Application Ser. No. 62/030,778, filed on Jul. 30, 2014. The entire contents of the foregoing are hereby incorporated by reference.

TECHNICAL FIELD

This invention relates to the use of methotrexate, e.g., repeated dosing or sustained-release formulations of methotrexate, for reducing risk of proliferative vitreoretinopathy (PVR) or epiretinal membranes (ERM) after surgical vitrectomy and/or scleral buckle to treat retinal detachment.

BACKGROUND

Retinal detachment (RD) is an important cause of sudden visual loss in the United States, with approximately 40,000 cases occurring annually. Permanent visual loss will result if treatment is delayed.

A retinal detachment is defined as the separation of the neurosensory retina from the retinal pigment epithelium (RPE). In the nonpathologic state, the retinal pigment epithelium is a continuous epithelial monolayer occluded by tight junctions, which maintain a strict separation of the underlying choroidal capillary beds from the photoreceptors of the sensory retina, thus forming the outer blood-retina barrier. Its functions include the nourishment of photoreceptors, elimination of waste products, and reabsorption of subretinal fluid.

The definitive treatment of retinal detachment is surgical repair. Multiple operative techniques are available to the treating retinologist, but the principles underlying treatment of retinal detachment remain the same: removal of fluid from the subretinal space, relief of any existing traction, and treatment and prophylaxis against the underlying cause for the ingression of fluid, whether it be due to a retinal break or an exudative process.

Proliferative vitreoretinopathy (PVR) is the most common cause for failure of retinal detachment surgery, a complication which occurs in 5-10% of all retinal detachment surgeries. PVR can also occur spontaneously in the absence of surgery. PVR is most likely to develop following repeated surgical instrumentation of the eye, following significant physiologic insult to the eye such as in trauma, as well as in retinal detachments complicated by multiple tears, giant tears, vitreous hemorrhage, or in eyes with uveitis.

A milder form of PVR, called macular pucker or epiretinal membrane (ERM), complicates the post-operative course of 20-30% of RD surgeries and half of these are so visually distorting that patients will require surgery. In addition, autopsy studies show that close to 75-80% of patients with RD surgery have histological evidence of proliferative membranes. This may explain why many patients do not achieve perfect vision postoperatively after RD surgery, yet do not have any clinically obvious ERMs. In addition, ERMs can also develop spontaneously.

No treatments to date have been found to be preventive against PVR or ERMs. Once PVR or ERMs develop, surgery is the only treatment.

SUMMARY

The present invention is based, at least in part, on the development of methods to treat and to reduce the risk of developing PVR or ERM.

Thus, in a first aspect the invention provides methods for treating or reducing the risk of proliferative vitreoretinopathy (PVR) or epiretinal membranes (ERM) in a subject. The methods include administering a plurality, e.g., ten or more, intravitreal injections of methotrexate over a period of at least one, two, three, or more months, given no more frequently than weekly.

In some embodiments, each injection provides a dose of 400 mcg in 0.1 ml methotrexate.

In some embodiments, the methotrexate is administered posterior to the limbus.

In some embodiments, the subject is undergoing an ocular surgical procedure that increases the subject's risk of developing ERM or PVR, e.g., a pars plana vitrectomy (PPV), Retinal Detachment (RD) surgery; ERM surgery; scleral buckle surgery; or a procedure in the other eye. In some embodiments, the subject requires a PPV to treat a rhegmatagenous retinal detachment secondary to trauma; preexisting proliferative vitreoretinopathy (e.g., grade C or higher); or for other indications associated with high risk condition for PVR development, e.g., giant retinal tears (giant retinal tears are defined as tears involving 90° or more of the circumference of the globe), retinal breaks larger than 3 disc areas, long-standing retinal detachments, or detachments associated with hemorrhage.

In some embodiments, a first injection is given at conclusion of the surgical procedure; eight weekly injections are given until postoperative month two; and a final tenth injection is given at postoperative month three.

In some embodiments, the methods include administering nine consecutive weekly injections, and a tenth injection three months after the first injection.

In some embodiments, the methods include administering additional injections monthly after the final, e.g., tenth, injection.

In some embodiments, the methods include administering one, two, three, four, five, six, seven, eight, or nine additional injections, e.g., monthly, after the tenth injection.

In another aspect, the invention provides methods for treating or reducing the risk of PVR or ERM in a subject. The methods include intravitreally administering a sustained release formulation of methotrexate over at least a three-month period.

In some embodiments, the sustained release formulation is or comprises a lipid-encapsulated formulation; multivesicular liposome (MVL) formulations of methotrexate (MTX); nano- or microparticles; polyion complex (PIC) micelles; or bioadhesive polymers. In some embodiments, the bioadhesive polymers comprise one or more of hydroxypropyl methylcellulose (HPMC), carboxymethylcellulose (CMC), polyacrylic acid (PAA), or hyaluronic acid (HA).

In a further aspect, the invention provides methods for treating or reducing the risk of PVR or ERM in a subject. The methods include implanting a device for sustained release of methotrexate over at least a three-month period into the eye of the subject.

In some embodiments, the device is non-biodegradable.

In general, in the methods described herein, the subject does not have cancer, e.g., does not have an ocular cancer, e.g., does not have ocular or B cell lymphoma. In some embodiments, the subject does not have uveitis. In some embodiments, the methods include determining that a subject has or is at risk of developing PVR or ERM, or is about to undergo a procedure with a high risk of PVR or ERM as a side effect, and selecting the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Proliferative vitreoretinopathy (PVR) is a common occurrence after retinal detachment surgery. PVR is a "scarring" condition that forms inside the eye after surgery, significant trauma, or even spontaneously. Its pathogenesis is the disruption of the retinal pigment epithelium layer, which is associated with inflammation, migration, and proliferation of cells to the (neural) retinal surface. Over the next 4-12 weeks, membranes on the surface of the retina proliferate, contract, and apply traction on the retina, which results in redetachment of the retina from the RPE. Once PVR is present and the retina detaches for a second time, it is unlikely that vision will be restored.

Pathobiology of Proliferative Vitreoretinopathy (PVR) and Epiretinal Membranes (ERM)

Epiretinal membranes (ERM) are caused by an abnormal proliferation of cells, e.g., retinal pigment epithelial (RPE) cells, glial cells, fibroblasts, and macrophages, on the surface of the retina, typically in response to ocular disease; the membranes tend to contract and cause puckering and thus distortion of the macula. See, e.g., Hiscott et al., Br J Ophthalmol. 68(10):708-15 (1984); Hiscott et al., Eye 16, 393-403 (2002); and Asato et al., PLoS One. 8(1): e54191 (2013).

Like ERM, PVR is an abnormal wound healing response of the vitreous and retina, a clinical syndrome where cells with proliferative capacity, driven by inflammatory mediators, multiply on the retinal surface, contract, and eventually cause recurrent retinal detachment (RD). The pathogenesis of PVR begins with the introduction of RPE cells into the vitreous cavity. These cells may be introduced at the time of the retinal tear itself or may be introduced iatrogenically such as through the use of cryotherapy or retinectomy. Studies from monkey eyes with PVR have also postulated that the introduction of Müller cells, as well as potentially fibrocytes, occur as well. Concomitant with the introduction of RPE cells is the introduction or upregulation of growth factors, including vascular endothelial growth factor (VEGF), platelet-derived growth factor (PDGF), fibronectin, transforming growth factor-beta (TGF-β), and other mediators. This process begins an autocrine loop where glial, RPE, and other cellular constituents proliferate and transdifferentiate into contractile myofibrocytes. On pathology, macrophages as well as fibroblasts are commonly identified in specimens of PVR.

It has also been proposed that, at this time of RPE disruption, inflammation plays an important role in the development of PVR. Cytokines IL-6, IL-1, TNF-alpha, and IFN-gamma have been identified in high concentrations in the vitreous in the early, proliferative stages of PVR, but they decrease to normal levels in the scarring phase. These cytokines are not present in eyes that do not develop PVR.

The use of a pharmacologic adjuvant to prevent PVR has been an elusive goal in ophthalmology. A general pharmacologic strategy employed in prior PVR studies has been the single intravitreal, intraoperative administration of a variety of agents, such as duanoribicin, 5-fluorouracil (5-FU), triamcinolone, low-molecular weight heparin, and naproxen.[10-15] Although the clearance of vitreally delivered drugs is dependent on a number of factors including the molecular weight of the drug, the status of the blood-retina barriers, contents of the vitreous cavity, etc., it is likely that those drugs used in these prior PVR studies were cleared from the eye within days after their administration. In contrast, PVR does not become a clinically appreciable, pathologic entity until at least 6-8 weeks after surgery.

Methotrexate

Methotrexate is a non-naturally occurring chemically also known as N-[4-[[(2,4-diamino-6-pteridinyl) methyl] methylamino] benzoyl]-L-glutamic acid. A folate analog, methotrexate is thought to act as an anti-proliferative agent by reversibly inhibiting dihydrofolate reductase, which prevents dihydrofolate from being reduced to tetrahydrofolate, which is used in the synthesis of purine nucleotides.

Mechanisms of anti-inflammatory action are less clear, although mechanisms that have been proposed include its ability to enhance the extracellular concentration of adenosine, suppression of pro-inflammatory cytokines, inducement of apoptosis of activated T cells, and suppression of intracellular adhesion by activated T cells.

In some embodiments, the methotrexate is formulated for repeated injection, e.g., in Balanced Salt Solution from 25 mg vials to a sterile, single-use dose of 400 mcg/0.1 ml.

In some embodiments, the methotrexate is formulated for sustained release. A number of sustained release formulations of methotrexate are known in the art, including but not limited to biodegradable implants such as lipid-encapsulated formulations, e.g., Depo/Methotrexate, as described in Bonetti et al., Cancer Chemother Pharmacol 33:303-306 (1994) and Chatelut et al., J Pharm Sci. 1994 March; 83(3):429-32; multivesicular liposome (MVL) formulations of methotrexate (MTX), e.g., as described in WO02011143484; nano- or micropartricules, e.g., alpha-lactalbumin microparticles, e.g., as described in Vijayaragavan et al., Int J Pharm Res 3(1):39-44 (2011) or nanoparticles of conjugated methotrexate-human serum albumin as described in Taheri et al., J Nanomaterials 2011 (dx.doi.org/10.1155/2011/768201); polyion complex (PIC) micelles; bioadhesive polymers such as hydroxypropyl methylcellulose (HPMC), carboxymethylcellulose (CMC) and polyacrylic acid (PAA) derivatives, as well as hyaluronic acid (HA), e.g., Lacrisert (Aton Pharma), which is a soluble hydroxy propyl cellulose ocular insert.

Alternatively or in addition, sustained release can be achieved using a sustained-release device such as intravitreal implants, e.g., as described in Palakurthi et al., Current Eye Research, 35(12):1105-1115 (2010) or similar to the Retisert (Bausch & Lomb), Ozurdex (Allergan); or non-biodegradable implants, e.g., similar to Iluvien (Alimera) or Vitrasert (Bausch & Lomb) implants; the I-vation platform (SurModics Inc.). See also Lee et al., Pharm Res. 27(10): 2043-53 (2010); Haghjou et al., J Ophthalmic Vis Res. 6(4):317-329 (2011); Kim et al., Invest. Ophthalmol. Vis. Sci. 45(8):2722-2731 (2004); and Velez and Whitcup, Br J Ophthalmol 83:1225-1229 (1999).

Subjects

The methods described herein can be used to prevent (reduce the risk of) PVR or ERM in patients, e.g., in patients requiring pars plana vitrectomy (PPV), e.g., for rhegmatagenous retinal detachment secondary to trauma; for patients requiring PPV for preexisting proliferative vitreoretinopathy grade C or higher; and/or for patients with retinal detachments requiring PPV for other indications associated with high risk condition for PVR development, e.g., giant retinal tears (giant retinal tears are defined as tears involving 90° or more of the circumference of the globe), retinal breaks larger than 3 disc areas, long-standing retinal detachments, or detachments associated with hemorrhage.

Other uses of sustained methotrexate in the eye in addition to PVR include the following:

Prevention of Epiretinal Membranes after Retinal Detachment (RD) Surgery

Approximately 20-30% of RD cases develop clinically perceptible ERMs. Half of these are so visually distorting that patients will require surgery. In addition, autopsy studies show that close to 75-80% of patients with RD surgery have some degree of proliferative of membranes. This may explain why many patients do not achieve perfect vision postoperatively after RD surgery, yet do not have any ERMs grossly perceptible to the human eye.

Prevention of ERMs that Develop Spontaneously

ERMs can develop spontaneously, which then requires surgery. If a subject developed an ERM in one eye, implanting a device to prevent ERMs in the other eye could prevent development in that eye.

Prevention of Secondary ERM after ERM Surgery

For patients who develop ERMs, these can be removed but some reoccur and require reoperation. Leaving an implant could prevent the recurrent ERM.

The methods described herein can include identifying and/or selecting a subject who is in need of treatment to prevent the development of PVR or ERM as a result of a condition listed above (e.g., selecting the subject on the basis of the need of treatment as a result of a condition listed above, e.g., an increased risk of developing PVR or ERM as a result of a condition listed above). In some embodiments, the subjects treated with a method described herein do not have ocular cancers, e.g., do not have lymphoma (e.g., B cell lymphoma), and/or do not have uveitis.

The presentation of PVR clinically encompasses a wide phenotype. PVR can vary from a mild cellular haze (Grade A) to thick, fibrous membranes that cause the characteristic stiffened funnel of the detached retina (Grade D). A number of grading systems are in use, see, e.g., Ryan, *Retina*, 5th ed (Elsevier 2013); Retina Society Terminology Committee. The classification of retinal detachment with proliferative vitreoretinopathy. Ophthalmology 1983; 90:121-5 (1983); Machemer R, Aaberg T M, Freeman H M, et al. Am J Ophthalmol 112:159-65 (1991); Lean J, Irvine A, Stern W, et al. Classification of proliferative vitreoretinopathy used in the silicone study. The Silicone study group. Ophthalmology 1989; 96:765-771. In some embodiments the methods include identifying, selecting, and/or treating a subject who has a low grade (e.g., Grade A or Grade 1) PVR, or who has ERM. In some embodiments, the methods include monitoring the subject for early signs of the development of PVR or ERM, i.e., the presence of a "vitreous haze" indicating a cellular proliferation (which may eventually develop into an organized sheet), and administering one or more doses of MTX as described herein. Although early Grade A PVR vs. an early ERM may be difficult to distinguish from one another, eventually untreated PVR will progress; ERMs will cause a mild traction on the macula resulting in metamorphopsia but will not cause detachment of the retina, whereas untreated PVR will cause detachment and eventually result in a funneled, atrophic retina. The methods can also be used to treat subjects without present signs of PVR but who are at risk for PVR or ERMs.

Methods of Treating or Reducing Risk of PVR or ERM

The methods described herein include the use of methotrexate in subjects who are at risk of developing a first or recurring PVR or ERM, e.g., a subject who is undergoing RD surgery or ERM surgery, as described above, and in subjects who have PVR or ERM or who are at risk for developing PVR or ERMs. In some embodiments, the methods described herein include the use of methotrexate in subjects who have undergone, are undergoing, or will undergo a pars plana vitrectomy (PPV) or scleral buckle (SB). In some embodiments, the methods include performing a PPV, RD surgery, or ERM surgery. Methods for performing these surgeries are known in the art; for example, typically, PPV is performed under local or general anesthesia using three, 23 or 20 gauge sclerotomy ports. Any present epiretinal membranes can be dissected, e.g., using a membrane pick and forceps. Intraoperative tissue staining, perfluorocarbons, cryopexy, endolaser, scleral buckling, and lensectomy can also be performed as needed. Standard tamponading agents can be used, e.g., silicone oil or gas.

The methods described herein include the use of an effective amount of methotrexate. An "effective amount" is an amount sufficient to effect beneficial or desired results, e.g., the desired therapeutic effect (i.e., a prophylactically effective amount that reduces the risk of developing PVR or ERM). An effective amount can be administered in one or more administrations, applications or dosages. A therapeutically effective amount of methotrexate can be, e.g., 400 µg/0.1 ml per injection, e.g., with at least ten injections, giving a cumulative dose of 4,000 µg over ten injections; in some embodiments, the methods include giving more than ten injections, for a cumulative dose of more than 4,000 μg. In some embodiments, the methods include giving fewer than ten injections, for a cumulative does of less than 4,000 ug. The compositions can be administered one from one or more times per day to one or more times per week to one or more times per month; including once every other day. The skilled artisan will appreciate that certain factors may influence the dosage and timing required to effectively treat a subject, including but not limited to the severity of the disease or disorder, previous treatments, the general health and/or age of the subject, and other diseases present.

In some embodiments, intravitreal methotrexate injections are performed aseptically after the topical application of anaesthesia and an antiseptic agent, e.g., 5% povidone iodine, to the conjunctival sac. In some embodiments, each subject receives an intravitreal injection of methotrexate, e.g., 400 mcg/0.1 ml methotrexate, 3.0 to 3.5 mm posterior to the limbus, depending on lens status, with a 30-gauge needle.

Figure 1:
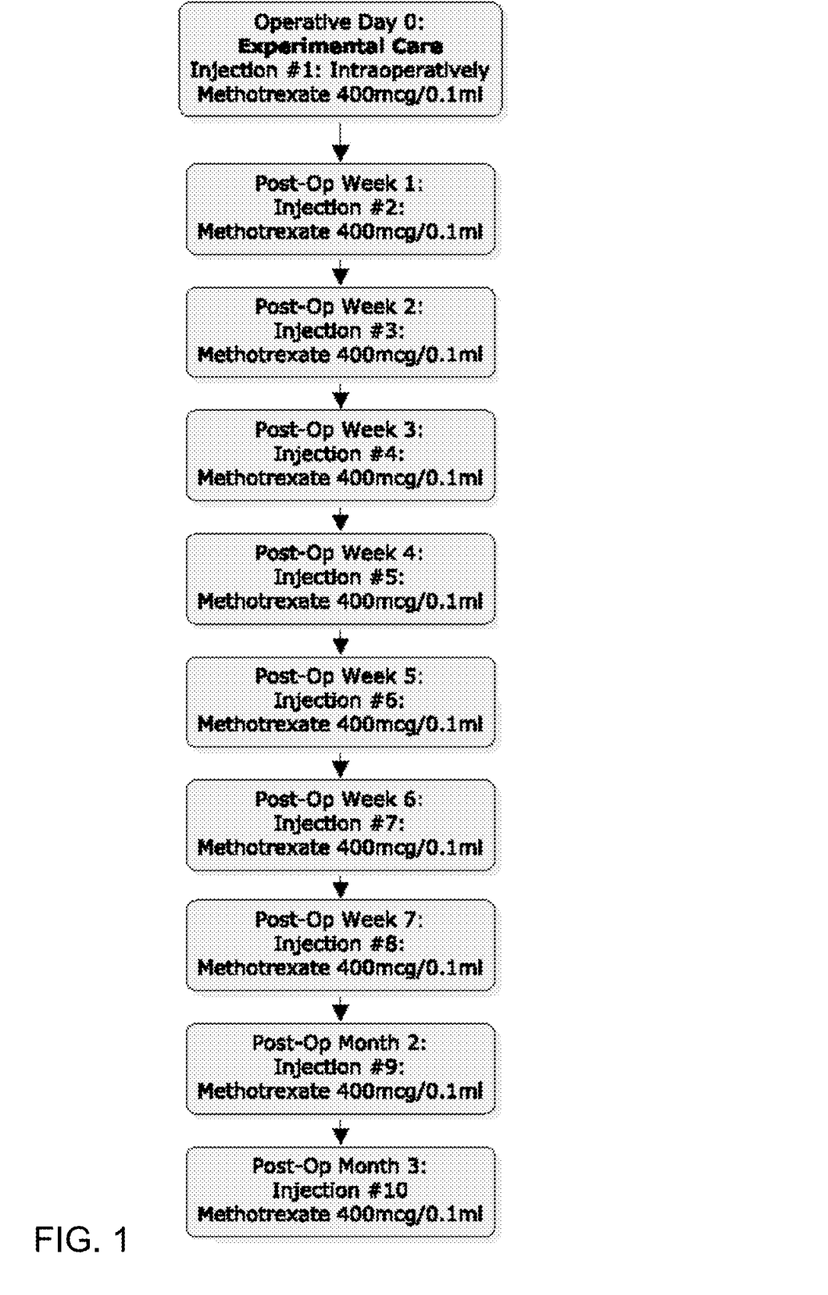
FIG. 1 is a flowchart showing an exemplary treatment protocol using the present methods.

In some embodiments, the subjects receive multiple intravitreal injections of methotrexate during their post-operative period. The first injection can be administered intraoperatively; subsequently, injections can be administered on post-operative (post-op) weeks 1, 2, 3, 4, 5, 6, 7, and 8, and on post-op month 3, for a total of 10 injections. See, e.g., FIG. 1. In some embodiments, the methods include administering the methotrexate in ten doses, or ten or more doses, or less than ten doses, over a three-month period or longer, and injections would be given no more frequently than weekly. In some embodiments, the methods include additional doses at weekly, biweekly, or monthly frequency thereafter for an additional one, two, three, four, five, six, seven, eight, nine, ten, 11, or 12 months thereafter. In some embodiments the methods include ten doses over three months as shown in FIG. 1, with an optional additional one or more doses at monthly intervals thereafter for an additional one, three, six, or more months thereafter.

In some embodiments, the subjects receive a sustained release implant, e.g., as described above, that will release MTX over time, e.g., over a week, two weeks, a month, two months, three months, six months, or a year. In some embodiments, the methods include administering subsequent implants to provide MTX administration for at least six months, one year, two years, or more.

EXAMPLES

The invention is further described in the following examples, which do not limit the scope of the invention described in the claims.

Example 1

Sustained Methotrexate in the Silicone Filled Postoperative Eye at High Risk for Proliferative Vitreoretinopathy We hypothesized that the administration of multiple, intravitreal methotrexate injections into eyes with high-risk features for post-operative proliferative vitreoretinopathy (PVR) development will have improved visual outcomes, higher anatomic final reattachment rates, decreased reoperation rates, and decreased occurrence of PVR at 4 months postoperatively.

We have performed a small pilot study in 10 patients with retinal detachment whom had high-risk clinical factors for developing PVR.

Patients 18 years to 89 years old of both genders were eligible for this study if they required pars plana vitrectomy (PPV) for rhegmatagenous retinal detachment secondary to trauma, PPV for preexisting proliferative vitreoretinopathy grade C or higher, or if they had retinal detachments requiring PPV for other indications associated with high risk condition for PVR development, i.e.: giant retinal tears (Giant retinal tears are defined as tears involving 90° or more of the circumference of the globe), retinal breaks larger than 3 disc areas, long-standing retinal detachments, detachments associated with hemorrhage.

The PPV was performed under local or general anesthesia using three, 23 or 20 gauge sclerotomy ports. Any present epiretinal membranes were dissected using a membrane pick and/or forceps. Intraoperative tissue staining, perfluorocarbons, cryopexy, endolaser, scleral buckling, and lensectomy were performed as needed. Either silicone oil or gas was used as the tamponading agent.

Routine post-operative visits, which involve a dilated funduscopic examination, occurred on post-operative day 1, 7, month 1, month 2, and month 3. Patients return to the operating room after three months for silicone oil removal and were seen in clinic 4 months after the original surgery.

In addition to receiving the above-described standard of care, patients received multiple intravitreal methotrexate injections during their post-operative period. The first injection was administered intraoperatively and subsequently was injected on post-op week 1,2,3,4,5,6,7,8 and on post-op month 3, for a total of 10 injections. Intravitreal methotrexate injections were performed aseptically after the topical application of anaesthesia and 5% povidone iodine to the conjunctival sac. Each patient received an intravitreal injection of 400 mcg/0.1 ml methotrexate, 3.0 to 3.5 mm posterior to the limbus, depending on lens status, with a 30-gauge needle.

After injection, patients were monitored for adverse events, including a full-dilated funduscopic examination.

Demographics and Pre-Operative Vision

Eight men and two women enrolled into the study (Table 1). The age of patients ranged from 18 to 63. Two patients (#4 & #9) were enrolled with traumatic retinal detachment (total retinal detachment, 360 degree giant retinal tear, and retina incarcerated in scleral wound after open globe injury). The remaining 8 patients had had multiple (average 2.5) prior retinal detachments secondary to proliferative membranes. One patient (MTX08M) had significant baseline retinal comorbidity with high pathologic myopia, staphyloma, atrophy, lattice and paving stone in the operative eye. The median pre-operative visual acuity was Hand Motions at 2 feet.

Operative Details

Operative details of each patient are provided in Table 2. Operative time was recorded as a surrogate for surgical complexity. All patients underwent vitrectomy, extensive membrane peeling, relaxing retinectomy, perfluorocarbon liquid, endolaser, and silicone oil injection. The four subjects previously surgically intervened on had buckles that were still providing adequate indentation of the globe and were therefore left in place.

Visual and Anatomical Results

Despite the extremely poor visual and anatomic prognosis of all the subjects enrolled in the study, no subjects developed PVR while receiving methotrexate during the three-month treatment protocol. Interestingly, one of the trauma patients (#4) experienced massive PVR two weeks after completion of the injection protocol (at 3½ months postoperatively), but weekly examination during the study had shown no evidence of proliferating cells; this is extremely unusual and may be accounted for by the presence of methotrexate for three months and its subsequent absence. This patient required re-operation. Two other subjects developed reaccumulation of fluid under the retina requiring re-operation, but no membranes were appreciated.

Safety and Adverse Events

Adverse events observed are reported in Table 3. All subjects experienced a degree of conjunctival hyperemia, consistent with the use of silicone oil. Superficial punctuate keratopathy (SPK) was observed in one asymptomatic patient at a single clinical exam. Examination one week later showed a normal corneal surface and no further sequalae were observed. Follow up duration in our 10 patients ranged from 4 months to 39 months, with a median follow up time of 25 months. Even after months to years of follow up data, no significant adverse events were observed. Visual acuity and intraocular pressure at the last follow up visit was similar in all patients to the visual acuity and pressure observed at post-operative month 4, at the conclusion of the study period, suggesting good long term safety.

In addition, in the same patient who experienced SPK, elevated intraocular pressure was documented (44 mm Hg by Goldmann Tonometry) at a single examination. Per patient report, she had been taking Flonase (fluticasone nasal) "many times per day" and had been taking Pred Forte drops QID, although she had been instructed to take Pred Forte BID. Her pressure was normalized in the exam room with topical therapy. The intravitreal injection was administered as scheduled, and she was discharged from clinic with normal pressure. She was given a prescription for Alphagan and Xalatan with plans to follow up with the Glaucoma service. No further elevated pressures were observed during the course of the study or in follow up, suggesting that her transient elevated pressure was most likely due to excessive steroid use as suspected. Patient MTX08M ended the study with NLP vision. He had a history in the operative eye of pathological myopia, staphyloma, atrophy, lattice, and pave stoning. One month after his surgery (his third intravitreal surgery in that eye and the study surgery date), disc pallor was noted. Optical coherence tomographic pictures of that retina before and after had noted disorganized laminae, secondary to his underlying retinal disease. His vision at this was noted to be LP. He continued to receive injection with limited improvement in his vision and noted to be NLP at the final visit.

In addition to the excellent anatomical results seen, with virtually no PVR developing during the study protocol, the protocol was associated with excellent visual results. The median post-operative visual acuity was 20/200. This is notable because although one other group has used methotrexate in eyes with a wide variety of conditions, including PVR, no one has previously demonstrated improved outcomes. Hardwig et al. injected methotrexate intravitreally of varying doses into 5 patients, however, only one patient had any improved vision and there was no change in visual acuity for the group (Hardwig et al., Retina 28:1082-1086 (2008)). In addition, this study did not attempt to validate efficacy. Also, in 2006 Hardwig et al. injected 1 dose of methotrexate into the anterior chamber of one patient with PVR, but not into the intravitreal space as described herein (Hardwig et al., Am J Ophthalmol 2006; 142:883-885 (2006)).

The present results are very encouraging and are unlikely explained by chance. The patients who have received 10 intravitreal methotrexate injections have done remarkably well given the severity of their condition, as we intentionally selected patients who were at the highest risk for PVR.

Example 2

Sustained Methotrexate Inhibits the Growth of Proliferative Vitreoretinopathy in Vitro We hypothesized that methotrexate would inhibit human proliferative vitreoretinopathy (PVR) cells in culture. PVR membranectomy was performed in patients undergoing retinal detachment repair secondary to PVR. Using cellular separation techniques, cellular constituents of the PVR membranes were separated from the extracellular matrix membranes. 30,000 cells per well were placed into a standard 12 welled plate. All 12 wells received endothelial cell growth medium with supplemental growth factors. Four arms were designated consisting of three wells each. The first arm served as a control receiving the standard growth medium but no other intervention. The remaining wells were designated as treatment arms. The second arm of three wells served as the first treatment arm and exposed the cells to 400 micrograms of methotrexate. The third and fourth arms of three wells each exposed the cultured cells to 200 and 100 micrograms, respectively, of methotrexate.

Figure 2A:
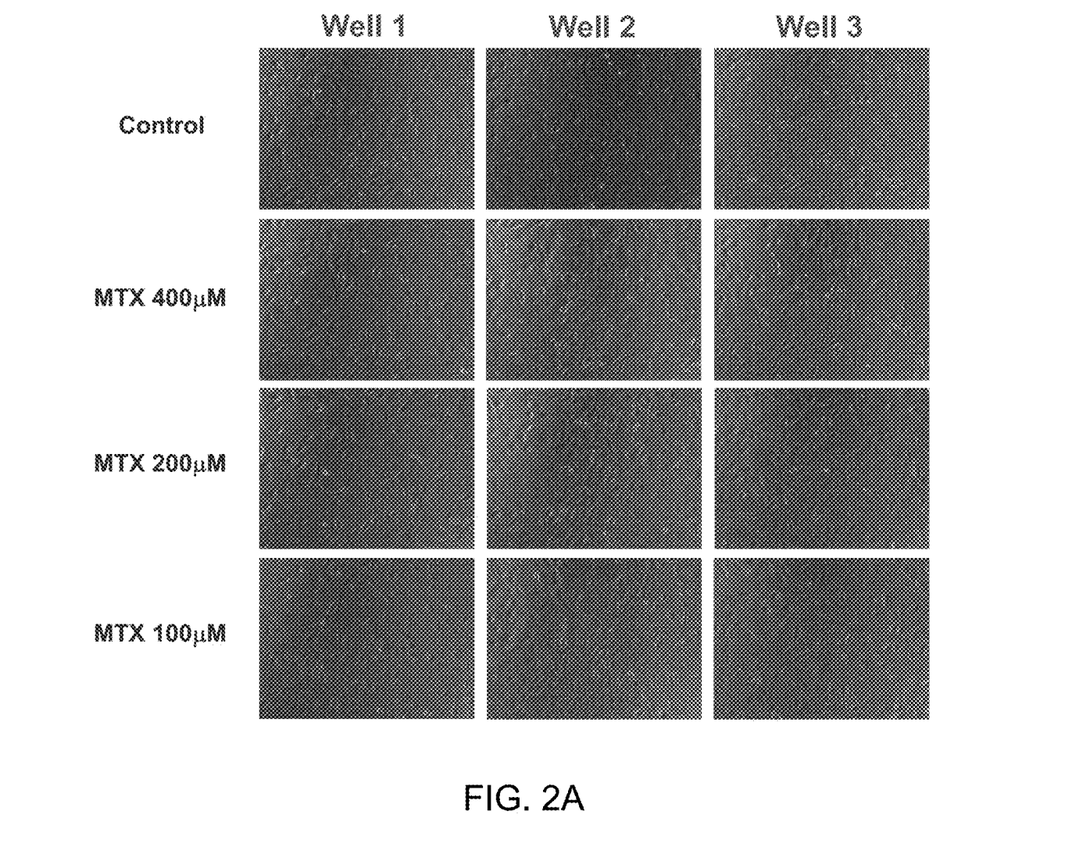
FIGS. 2A-2C are each sets of nine images of human PVR cells plated into 12 wells with 30,000 cells per well showing that methotrexate inhibited proliferation of human proliferative vitreoretinopathy (PVR) cells in culture. The cells were treated with 100 µM, 200 µM, or 400 µM Methotrexate (MTX) as indicated, and the images were taken after 72 hours (2A), 1 week (2B) or 2 weeks (2C). At 72 hours (2A), the photomicrograph showed similar epithelioid morphology and limited confluence across the control plates (top row), as well as the three methotrexate concentrations (rows 2-4). At 1 week (2B), the control plates (row 1) showed a uniform, confluent cellular sheet whereas rows 2-4, which were exposed to methotrexate 400, 200, and 100 respectively, showed growth inhibition and lack of confluency, and were less epithelioid in appearance. At 2 weeks, the control plates (row 1) continued to be a uniform, confluent cellular sheet, whereas rows 2-4, exposed to methotrexate 400, 200, and 100 respectively, continued to have inhibited growth and lack of confluency.
Figure 2B:
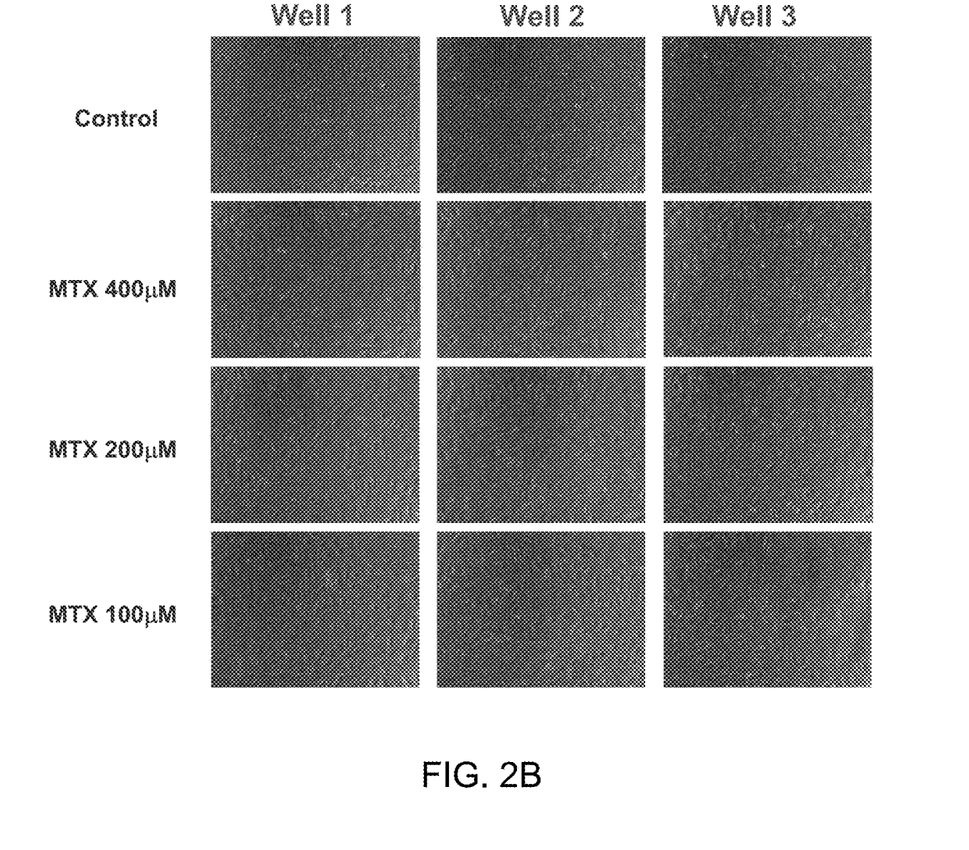
Figure 2C:
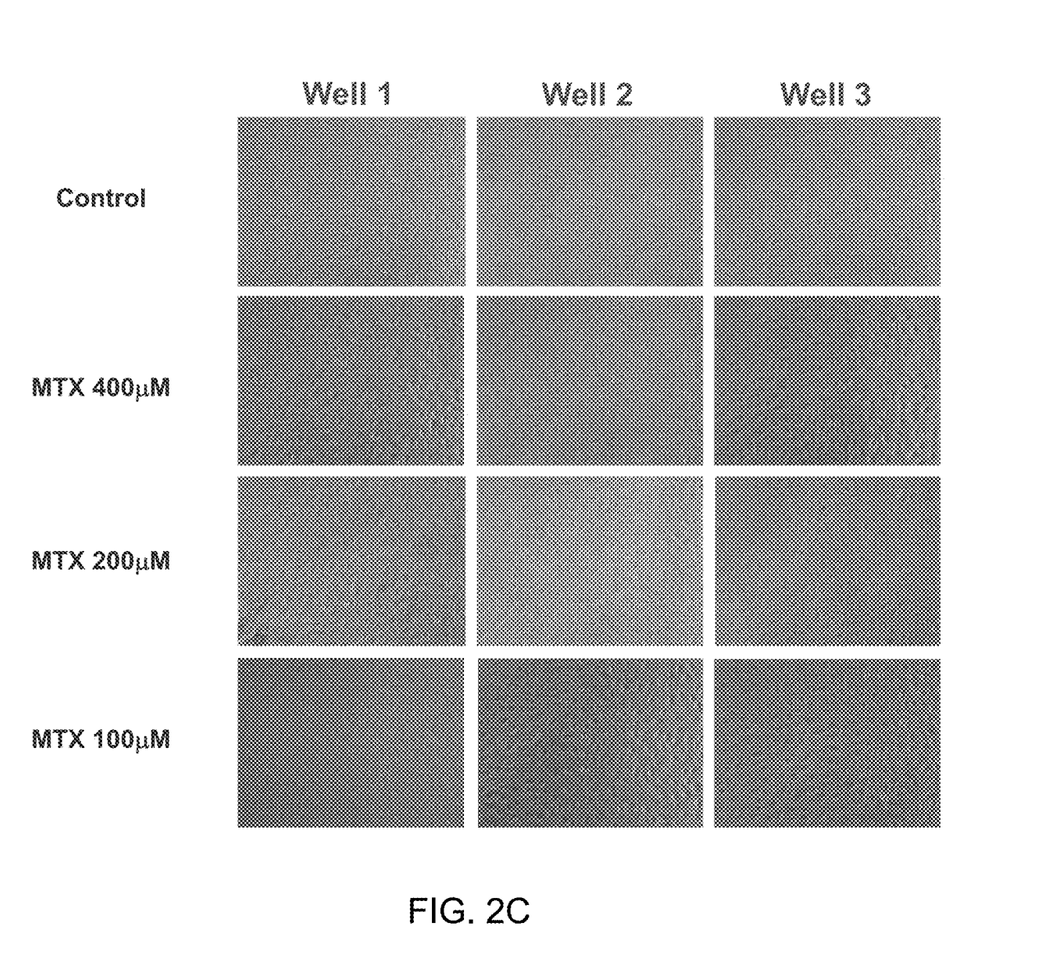

At 72 hours, similar growth of PVR cells with typical epithelioid morphology and limited confluence was observed (FIG. 2a). One week after seeding (FIG. 2b) the PVR control cells demonstrated a confluent cellular sheet whereas cells exposed to methotrexate at all concentrations demonstrated growth inhibition, lack of confluency, and were less epithelioid in appearance. At two weeks (FIG. 2C), inhibition of cellular confluency continued whereas the control plates continued to proliferate.

TABE 1

Patient demographics

| | studyid | Age | Male | Race | Critieria for entry | Childbearing potential | Ocular comorbidities | Previous number of surgeries attempted to repair RD |
|---|---|---|---|---|---|---|---|---|
| Patients enrolled in year 1 | MTX01F | 47 | No | White | PVR Grade C | No | none | 3 |
| | MTX02M | 60 | Yes | White | PVR Grade C | No | none | 3 |
| | MTX03M | 56 | Yes | White | PVR Grade C | No | lattice, mild cataract | 3 |
| | MTX04M | 25 | Yes | White | RD associated with open globe injury | No | Marginal lid laceration of right lower lid with canilicular involvement | 0 |
| | MTX05M | 29 | Yes | White | PVR Grade C | No | subluxated lens OS, lens removal age 4, diagnosed glaucoma age 11, post capsule removal age 17 subluxated lens OD, lens | 2 |

TABLE 1-continued

Patient demographics

|  | studyid | Age | Male | Race | Critieria for entry | Childbearing potential | Ocular comorbidities | Previous number of surgeries attempted to repair RD |
|---|---|---|---|---|---|---|---|---|
| Patients enrolled in year 2 | MTX06M | 54 | YES | White | PVR Grade C | No | removal age 17 none | 3 |
|  | MTX07M | 57 | YES | White | PVR Grade C | No | none | 2 |
|  | MTX08M | 63 | Yes | White | PVR Grade C | No | High Pathologic myopia; staphyloma OU; atrophy OU; lattice and paving stone OS | 2 |
|  | MTX09M | 53 | Yes | White | RD associated with open globe injury | No | none | 0 |
|  | MTX10F | 18 | NO | White | PVR Grade C | Yes, 2 methods of contraception + pregnancy test prior to every injection | s/p 5 prior strabismus surgeries | 2 |

TABLE 2

Clinical results

|  | studyid | Visual Acuity, initial | Visual Acuity, Post-op month 4 | Initial IOP | Final IOP | Injections | Detachments | Last follow up date | Total months of follow up | Visual acuity at last follow up | IOP at last follow up |
|---|---|---|---|---|---|---|---|---|---|---|---|
| Patients enrolled in year 1 | MTX01F | HM | 20/200 | 22 | 13 | 10 | 0 | Jul. 9, 2015 | 39 | 20/150 | 12 |
|  | MTX02M | 640 | 20/320 | 12 | 12 | 10 | 0 | May 20 2015 | 38 | 20/500 | 15 |
|  | MTX03M | HM | 20/200 | 9 | 12 | 10 | 0 | Jul. 14, 2015 | 39 | 20/300 | 16 |
|  | MTX04M | LP | 20/160 | 10 | 9 | 10 | 0* | Jul. 1, 2015 | 37 | HM | 9 |
|  | MTX05M | 600 | 20/200 | 11 | 10 | 10 | 0 | Dec. 3, 2015 | 4 | 20/200 | 9 |
| Patients enrolled in year 2 | MTX06M | LP | 20/252 | soft | 8 | 10 | 0 | Jul. 1, 2015 | 27 | CF | 9 |
|  | MTX07M | HM | 20/200 | 12 | 12 | 10 | 0 | Apr. 8, 2015 | 24 | CF | 22 |
|  | MTX08M | CF | NLP | 14 | 15 | 10 | 0 | Sep. 17, 2014 | 15 | NLP | 14 |
|  | MTX09M | LP | 20/65 | soft | 9 | 10 | 0 | Apr. 29, 2015 | 22 | 20/70 | 16 |
|  | MTX10F | HM | CF | 15 | 13 | 9 | 0 | Mar. 24, 2015 | 16 | CF | 14 |

*Massive PVR membranes developed two weeks after the final injection of methotrexate, despite there being no PVR in the preceding three months
Injections: Total number of injections of methotrexate 400 mcg/0.1 ml
Detachments: Number of detachments due to PVR during study period

TABLE 3

Adverse events observed in subjects

|  | studyid | Conjunctival hyperemia | Superficial Punctate Keratopathy | Elevated intraocular pressure | NLP | Reoperations required | Date of reoperation | Indication for reoperation |
|---|---|---|---|---|---|---|---|---|
| Patients enrolled in year 1 | MTX01F | 7 | 1 | 1 | 0 | 0 | — | — |
|  | MTX02M | 7 | 0 | 0 | 0 | 0 | — | — |
|  | MTX03M | 5 | 0 | 0 | 0 | 0 | — | — |
|  | MTX04M | 4 | 0 | 0 | 0 | 1 | Post-op month 4 | Outside the injection period (post-op month 3.5), significant PVR was seen. Patient was taken to the OR to peel membranes and remove traction from the retina. |
|  | MTX05M | 7 | 0 | 0 | 0 | 1 | Post-op month 2.5 | Persisitent sub-retinal fluid, no membranes |
| Patients enrolled in year 2 | MTX06M | 5 | 0 | 0 | 0 | 0 | — | — |
|  | MTX07M | 4 | 0 | 0 | 0 | 0 | — | — |
|  | MTX08M | 6 | 0 | 0 | 1 | 0 | — | — |
|  | MTX09M | 6 | 0 | 0 | 0 | 0 | — | — |
|  | MTX10F | 5 | 0 | 0 | 0 | 0 | — | — |

REFERENCES

1. Frenkel S, Hendler K, Siegal T, et al. Intravitreal methotrexate for treating vitreoretinal lymphoma: 10 years of experience. British Journal of Ophthalmology 2008; 92:383-388.
2. Fishburne B C, Wilson D J, Rosenbaum J T, Neuwelt E A. Intravitreal methotrexate as an adjunctive treatment of intraocular lymphoma. Arch Ophthalmol 1997; 115:1152-1156.
3. de Smet M D, Vancs V S, Kohler D, et al. Intravitreal chemotherapy for the treatment of recurrent intraocular lymphoma. British Journal of Ophthalmology 1999; 83:448-451.
4. Mietz H, Heimann K. Onset and recurrence of proliferative vitreoretinopathy in various vitreoretinal disease. British Journal of Ophthalmology 1995; 79:874-877.
5. Pastor J C, la Rúa de E R, Martin F. Proliferative vitreoretinopathy: risk factors and pathobiology. Progress in Retinal and Eye Research 2002; 21:127-144.
6. Hardwig P W, Pulido J S, Erie J C, et al. Intraocular Methotrexate in Ocular Diseases Other Than Primary Central Nervous System Lymphoma. Am J Ophthalmol 2006; 142:883-885.
7. Hardwig P W, Pulido J S, Bakri S J. The safety of intraocular methotrexate in silicone-filled eyes. Retina 2008; 28:1082-1086.
8. Velez G, Yuan P, Sung C, et al. Pharmacokinetics and toxicity of intravitreal chemotherapy for primary intraocular lymphoma. Arch Ophthalmol 2001; 119:1518-1524.
9. Creten O, Spileers W, Stalmans P. Systemic resorption of 5-fluorouracil used in infusion fluid during vitrectomy. Bull Soc Belge Ophtalmol 2007:37-41.
10. Cheema R A, Peyman G A, Fang T, et al. Triamcinolone acetonide as an adjuvant in the surgical treatment of retinal detachment with proliferative vitreoretinopathy. Ophthalmic Surg Lasers Imaging 2007; 38:365-370.
11. Ahmadieh H, Feghhi M, Tabatabaei H, et al. Triamcinolone Acetonide in Silicone-Filled Eyes as Adjunctive Treatment for Proliferative Vitreoretinopathy. Ophthalmology 2008; 115:1938-1943.
12. Yang C S, Khawly J A, Hainsworth D P, et al. An intravitreal sustained-release triamcinolone and 5-fluorouracil codrug in the treatment of experimental proliferative vitreoretinopathy. Arch Ophthalmol 1998; 116:69-77.
13. Chen E P, Steinhorst U H, Samsa G P, et al. The effect of combined daunorubicin and triamcinolone acetonide treatment on a refined experimental model of proliferative vitreoretinopathy. Investigative Ophthalmology & Visual Science 1992; 33:2160-2164.
14. Munir W M, Pulido J S, Sharma M C, Buerk B M. Intravitreal triamcinolone for treatment of complicated proliferative diabetic retinopathy and proliferative vitreoretinopathy. Can J Ophthalmol 2005; 40:598-604.
15. Chandler D B, Rozakis G, de Juan E, Machemer R. The effect of triamcinolone acetonide on a refined experimental model of proliferative vitreoretinopathy. AJOPHT 1985; 99:686-690.
16. Montesinos M C, Yap J S, Desai A, et al. Reversal of the antiinflammatory effects of methotrexate by the nonselective adenosine receptor antagonists theophylline and caffeine: evidence that the antiinflammatory effects of methotrexate are mediated via multiple adenosine receptors in rat adjuvant arthritis. Arthritis Rheum 2000; 43:656-663.
17. Gerards A H, de Lathouder S, de Groot E R, et al. Inhibition of cytokine production by methotrexate. Studies in healthy volunteers and patients with rheumatoid arthritis. Rheumatology (Oxford) 2003; 42:1189-1196.
18. Genestier L, Paillot R, Fournel S, et al. Immunosuppressive properties of methotrexate: apoptosis and clonal deletion of activated peripheral T cells. J Clin Invest 1998; 102:322-328.
19. Seitz M, Zwicker M, Wider B. Enhanced in vitro induced production of interleukin 10 by peripheral blood mononuclear cells in rheumatoid arthritis is associated with clinical response to methotrexate treatment. J Rheumatol 2001; 28:496-501.
20. Johnston A, Gudjonsson J E, Sigmundsdottir H, et al. The anti-inflammatory action of methotrexate is not mediated by lymphocyte apoptosis, but by the suppression of activation and adhesion molecules. Clin Immunol 2005; 114:154-163.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has an open globe injury, the method comprising administering a plurality of intravitreal injections of methotrexate over a period of at least one, two, three, or more months, given no more frequently than weekly.

2. The method of claim 1, comprising administering ten or more intravitreal injections of methotrexate.

3. The method of claim 1, wherein each injection provides a dose of 400 mcg methotrexate.

4. The method of claim 1, wherein the methotrexate is administered posterior to the limbus.

5. The method of claim 1, wherein the subject is undergoing an ocular surgical procedure to treat the injury.

6. The method of claim 5, wherein the ocular surgical procedure is a pars plana vitrectomy (PPV).

7. The method of claim 6, wherein the subject requires a PPV to treat a rhegmatogenous retinal detachment secondary to trauma.

8. The method of claim 7, wherein the subject has a giant retinal tear, a retinal break larger than 3 disc areas, or a detachment associated with hemorrhage.

9. The method of claim 5, wherein:
a first injection is given at conclusion of the surgical procedure;
eight weekly injections are given until postoperative month two; and
a final tenth injection is given at postoperative month three.

10. The method of claim 1, comprising administering nine consecutive weekly injections, and a tenth injection three months after the first injection.

11. The method of claim 1, comprising administering additional injections after the tenth injection.

12. The method of claim 11, comprising administering one, two, three, four, five, six, seven, eight, or nine additional injections after the tenth injection.

13. The method of claim 12, wherein the additional injections are administered monthly.

14. A method of treating an open globe injury in a subject, the method comprising:
  identifying a subject who has an open globe injury and is undergoing an ocular surgical procedure to treat the open globe injury;
  administering to the subject a first injection of methotrexate at conclusion of the ocular surgical procedure;
  administering to the subject eight weekly injections until postoperative month two; and
  administering to the subject two, three, or four additional injections thereafter.

15. The method of claim 14, wherein the additional injections are administered biweekly.

16. The method of claim 14, comprising administering to the subject three additional injections.

17. The method of claim 14, comprising administering to the subject four additional injections.

18. The method of claim 17, wherein the four additional injections are administered biweekly for two months thereafter.

19. The method of claim 14, wherein the injections are intravitreal.

20. The method of claim 14, wherein each injection provides a dose of 400 mcg of methotrexate.

21. The method of claim 14, wherein the methotrexate is administered posterior to the limbus.

22. The method of claim 14, wherein the ocular surgical procedure is a pars plana vitrectomy (PPV).

* * * * *